US011041772B2

(12) United States Patent
Atkinson et al.

(10) Patent No.: US 11,041,772 B2
(45) Date of Patent: Jun. 22, 2021

(54) SENSOR DIFFUSION STACK MATERIALS FOR PRESSURE SENSING GLOVES AND METHODS INCORPORATING THE SAME

(71) Applicant: Toyota Motor Engineering & Manufacturing North America, Inc., Plano, TX (US)

(72) Inventors: Benjamin Atkinson, Lexington, KY (US); Caleb Rogers, Lexington, KY (US); Tyler Flood, Stamping Ground, KY (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 0 days.

(21) Appl. No.: 16/363,135

(22) Filed: Mar. 25, 2019

(65) Prior Publication Data

US 2020/0309625 A1    Oct. 1, 2020

(51) Int. Cl.
| | |
|---|---|
| *G01L 5/16* | (2020.01) |
| *B33Y 80/00* | (2015.01) |
| *A41D 31/18* | (2019.01) |
| *A41D 19/00* | (2006.01) |

(52) U.S. Cl.
CPC ............ *G01L 5/16* (2013.01); *A41D 19/0027* (2013.01); *A41D 31/18* (2019.02); *B33Y 80/00* (2014.12)

(58) Field of Classification Search
CPC ......... G01L 5/226; G01L 5/228; G01L 5/009; G01L 5/205
See application file for complete search history.

(56) References Cited

U.S. PATENT DOCUMENTS

| | | | | |
|---|---|---|---|---|
| 4,503,416 A | * | 3/1985 | Kim ....................... | B25J 13/081 |
| | | | | 178/18.05 |
| 5,322,290 A | * | 6/1994 | Minami .................. | A63B 53/14 |
| | | | | 473/201 |
| 6,037,703 A | * | 3/2000 | Kambe .................... | G01L 1/16 |
| | | | | 29/25.35 |

(Continued)

FOREIGN PATENT DOCUMENTS

| | | |
|---|---|---|
| CN | 204426804 U | 7/2015 |
| CN | 104951061 A | 9/2015 |

(Continued)

OTHER PUBLICATIONS

Extended European Search Report and Preliminary Opinion with notification transmittal dated Aug. 6, 2020 in related European Application No. 20165355.7 (11 pages total).

*Primary Examiner* — Tran M. Tran
(74) *Attorney, Agent, or Firm* — Dinsmore & Shohl LLP (57) ABSTRACT

A pressure sensing glove for measuring a force includes a sensor having a pair of contact layers and a pair of diffusion layers disposed between the pair of contact layers. The pair of contact layers distributes a force received along outer surfaces of the sensor across the pair of diffusion layers. The sensor further includes a sensing layer disposed between the pair of diffusion layers. The pair of diffusion layers normalizes the force received from the pair of contact layers across the sensing layer. The sensing layer receives the force at a plurality of locations across a surface area of the sensing layer to determine a resultant pressure applied to the sensor.

23 Claims, 5 Drawing Sheets

(56) References Cited

U.S. PATENT DOCUMENTS

| | | | |
|---|---|---|---|
| 6,049,327 A * | 4/2000 | Walker | G06F 3/014 345/158 |
| 6,121,869 A * | 9/2000 | Burgess | H01H 3/141 200/511 |
| 6,944,974 B2 * | 9/2005 | Falone | A41D 13/015 36/44 |
| 7,780,541 B2 | 8/2010 | Bauer | |
| 7,878,075 B2 * | 2/2011 | Johansson | G01L 5/228 73/862.046 |
| 9,301,563 B2 * | 4/2016 | Hardy | A41D 19/0031 |
| 9,345,424 B2 * | 5/2016 | Wang | A61B 5/103 |
| 9,480,582 B2 * | 11/2016 | Lundborg | A61F 2/70 |
| 9,529,433 B2 * | 12/2016 | Shankar | G06F 3/014 |
| 9,562,818 B1 | 2/2017 | Adamski et al. | |
| 9,846,482 B2 * | 12/2017 | Seth | G06F 3/014 |
| 9,863,823 B2 * | 1/2018 | McMillen | A43B 17/00 |
| 10,296,085 B2 * | 5/2019 | Hamm | G06F 3/0487 |
| 10,362,989 B2 * | 7/2019 | McMillen | G01L 1/18 |
| 10,485,280 B1 * | 11/2019 | DePriest | G06F 3/044 |
| 10,716,342 B2 * | 7/2020 | Markison | A41D 19/065 |
| 2002/0075232 A1 * | 6/2002 | Daum | G06F 3/014 345/158 |
| 2010/0154106 A1 * | 6/2010 | Hammons | B60N 2/522 2/455 |
| 2011/0214221 A1 * | 9/2011 | Munda | B32B 15/04 2/161.1 |
| 2013/0085394 A1 * | 4/2013 | Corbett, III | A61B 8/4455 600/462 |
| 2013/0197399 A1 | 8/2013 | Montgomery | |
| 2016/0377139 A1 * | 12/2016 | Vito | A63B 71/0054 267/141 |
| 2017/0303853 A1 | 10/2017 | McMillen | |
| 2018/0340847 A1 | 11/2018 | Tingrui et al. | |
| 2020/0093202 A1 * | 3/2020 | Bae | G06F 3/01 |

FOREIGN PATENT DOCUMENTS

| | | |
|---|---|---|
| CN | 205107889 U | 3/2016 |
| CN | 206714926 U | 12/2017 |
| CN | 207616561 U | 7/2018 |
| WO | 20180213937 A1 | 11/2018 |

* cited by examiner

SENSOR DIFFUSION STACK MATERIALS FOR PRESSURE SENSING GLOVES AND METHODS INCORPORATING THE SAME

TECHNICAL FIELD

The present specification generally relates to sensor systems and processes for detecting and measuring a pressure applied to a sensor, and more specifically, to a sensor stack design incorporating distribution and diffusion materials of varying densities for conveying an applied-force across a sensor to determine a resultant force.

BACKGROUND

Sensors may be utilized to collect pressure measurements applied thereto. For instance, gloves incorporating sensor technology may be utilized to collect representative pressure measurements experienced along an operator's hand when a force is received thereon. To improve an accuracy of the pressure measurements detected by a sensor, a size, position and/or geometry of the sensor disposed along and/or within a glove may be determined relative to a predetermined task to be performed by an operator of the glove. In instances where a predetermined task may generally involve encountering physical forces at various angles relative to the sensor (e.g., due to a natural curvature of an operator's hand (including curved finger and palm surfaces)), a physical force applied thereto may be received in a non-perpendicular direction relative to a planar surface of the sensor. Accordingly, a determination of a resultant pressure measurement may include inaccuracies due to the angle of the force received at the sensor. The potential inaccuracy in measuring the detected pressure at the sensor may be detrimental to the objective of identifying the magnitude of force received thereon.

SUMMARY

In one embodiment, a pressure sensing glove for measuring a force includes a sensor including a pair of contact layers and a pair of diffusion layers disposed between the pair of contact layers. The pair of contact layers distributes a force received along outer surfaces of the sensor across the pair of diffusion layers. The sensor further includes a sensing layer disposed between the pair of diffusion layers. The pair of diffusion layers normalizes the force received from the pair of contact layers across the sensing layer. The sensing layer receives the force at a plurality of locations across a surface area of the sensing layer to determine a resultant pressure applied to the sensor.

In another embodiment, a method includes receiving a force applied to a glove including a sensor at a location along an outer-contact layer of the sensor and distributing the force from the location along the outer-contact layer to a plurality of locations across the outer-contact layer. The method further includes receiving the forces from the plurality of locations of the outer-contact layer at a plurality of locations of an outer-diffusion layer of the sensor. The outer-diffusion layer is disposed beneath the outer-contact layer relative to the force received thereon. The method further includes normalizing the forces through the outer-diffusion layer at the plurality of locations across the outer-diffusion layer, and receiving the forces across a surface area of a sensing layer of the sensor. The sensing layer is disposed beneath the outer-contact layer and the outer-diffusion layer relative to the force received thereon.

In another embodiment, a glove apparatus includes a sensor including an outer layer positioned along a surface of the glove apparatus and configured to receive a force from the surface of the glove apparatus, the outer layer is further configured to distribute the force and normalize the distributed force therethrough. The glove apparatus includes an inner layer positioned adjacent to the outer layer and configured to receive a normal force in response to the outer layer receiving the force at the surface of the glove apparatus, the inner layer is further configured to distribute the normal force and normalize the distributed normal force therethrough. The glove apparatus further includes a sensing layer disposed between the outer layer and the inner layer, the sensing layer is configured to receive the normalized force from the outer layer and the normalized normal force from the inner layer to detect a resultant magnitude of the force received from the surface of the glove apparatus.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Glove systems may include one or more arrays (e.g., regions) of sensor assemblies positioned thereon designed to collectively detect a force received along the glove. By detecting a physical force applied to the sensor arrays of the glove, an operator of the glove may identify a resultant pressure endured at various locations along the operator's hand. With the pressure data detected by the sensor assemblies of the glove, an operator of the glove system may adjust a manner in performing a task (e.g., adjusting a physical position, geometry, and/or orientation of an operator's hand) as a result of analyzing said data to minimize the force endured along an operator's hand and thereby reduce instances of possible injury, discomfort, and/or unnecessary-expended labor when performing the task. To determine an appropriate method to perform a task, based on the forces applied to an operator's hand when performing the task, accurately measuring a resultant pressure is desirable. However, in some instances a resultant pressure measurement may vary relative to an actual force received along an operator's hand due to the varying angles in which the force is received along a palmar surface of the hand and/or a planar surface of the sensor assembly. Inaccuracies of measuring a force vector may provide challenges in accurately measuring a resultant pressure applied to an operator's hand and in determining an appropriate method in performing a task with the operator's hand.

The present disclosure relates generally to glove systems and methods that include sensor technology for detecting and measuring forces received along the glove. More specifically, the present disclosure relates to sensor assemblies of a glove system and methods that improve an accuracy of measuring a pressure received along the sensor assembly of the glove by including a plurality of layers of varying materials disposed about a core sensor layer of the sensor assembly. The plurality of layers disposed about the core sensor layer is particularly configured to distribute and normalize a force received along the sensor assembly. Providing a sensing system that distributes a force across a core sensor layer may assist in accurately measuring a resultant pressure calculated from a force applied thereto, and in particular forces having an angled orientation relative to a surface of the glove. The glove system may aid in determining an appropriate method, such as a physical position or orientation, in performing a task by detecting and measuring various forces received at an operator's hand at varying angles relative to a palmar surface of the operator's hand with accuracy by distributing and diffusing the force across the plurality of layers of the glove system for accurate detection.

Figure 1:
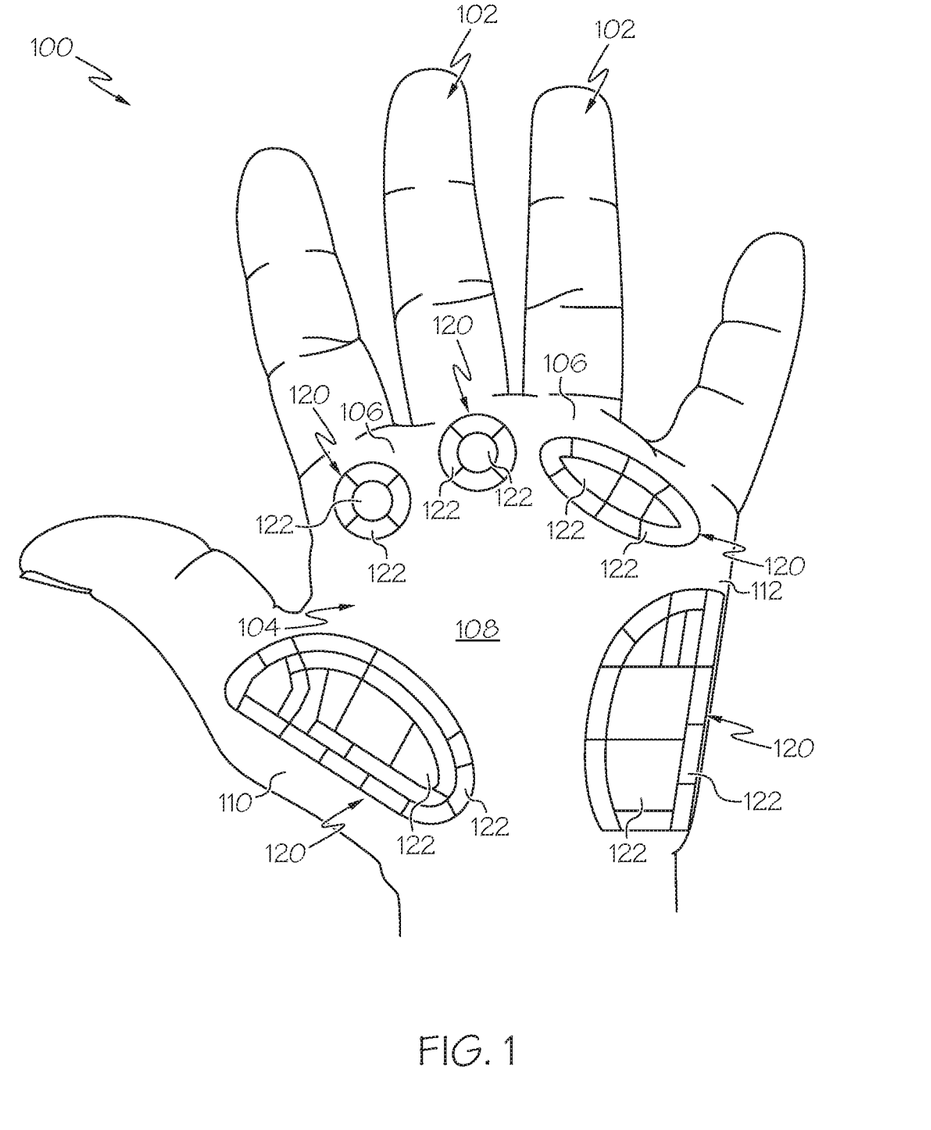
FIG. 1 schematically depicts an illustrative sensing glove system including a plurality of sensor regions along palmar surfaces of a glove according to one or more embodiments shown and described herein.

Referring now to the drawings, FIG. 1 depicts an illustrative glove system 100 including at least one finger surface region 102 and a palmar surface region 104. The palmar surface region 104 of the glove system 100 includes a palmar metacarpal region 106, a median palmar region 108, a hypothenar region 110, and a thenar region 112. The palmar surface region 104 of the glove system 100 includes one or more sensor arrays 120 positioned thereon, and in particular along one or more of the palmar metacarpal region 106, the median palmar region 108, the hypothenar region 110, and the thenar region 112. In the present example, the palmar surface region 104 includes three sensor arrays 120 positioned along the palmar metacarpal region 106, one sensor array 120 positioned along the hypothenar region 110 and one sensor array 120 positioned along the thenar region 112. The one or more sensor arrays 120 may be secured to and attached to the glove system 100 by various methods, including, but not limited to, printing the one or more sensor arrays 120 onto a fabric of the glove system 100, weaving the one or more sensor arrays 120 into a fabric of the glove system 100, adhesively securing the one or more sensor arrays 120 to the glove, and/or the like. It should be understood that additional and/or fewer sensor arrays 120 may be positioned along various anatomical regions of the palmar surface region 104 than those shown and depicted herein without departing from the scope of the present disclosure.

The one or more sensor arrays 120 of the glove system 100 include a plurality of sensing regions 122 positioned therein. In some embodiments, the plurality of sensing regions 122 of each of the one or more sensor arrays 120 are sized, shaped and positioned along the palmar surface region 104 relative to an intended-task to be performed with the glove system 100. In other words, a location and profile of the one or more sensor arrays 120, and the plurality of sensing regions 122 included therein, along the palmar surface region 104 of the glove system 100 may be determined based on a predetermined use of the glove system 100. Accordingly, the one or more sensor arrays 120 are sized and positioned along the corresponding regions 106, 108, 110, 112 of the palmar surface region 104 that generally receive a force load thereon when performing the predetermined task with an operator's hand. As will be described in greater detail herein, the one or more sensor arrays 120 may be positioned along the finger surface region 102 of the glove system 100 for instances where an operator's hand generally receives a force load thereon when performing a predetermined task. In addition to the one or more sensor arrays 120 being positioned along the glove system 100 at locations where a static, push load may be received during performance of a predetermined task, the one or more sensor arrays 120 may be further positioned along portions of the glove system 100, and in particular the palmar surface region 104, where transverse, slidable loads may be received that generate indirect forces along an operator's hand.

Still referring to FIG. 1, the plurality of sensing regions 122 of each of the one or more sensor arrays 120 are further sized, shaped and positioned along the palmar surface region 104 relative to a surface curvature of an operator's hand. In other words, a profile of the one or more sensor arrays 120, and the plurality of sensing regions 122 included therein, along the palmar surface region 104 of the glove system 100 may be determined based on a surface curvature of an operator's hand along the particular region 106, 108, 110, 112 of the palmar surface region 104 where the sensor array 120 is located. In the present example, the plurality of sensing regions 122 of the sensor arrays 120 located along the palmar metacarpal region 106 are sized and shaped relative to the curvature and size of the palmar metacarpal region 106. Accordingly, the plurality of sensing regions 122 of the sensor arrays 120 located along the palmar metacarpal region 106 are relatively small and circular due to a corresponding contour of the palmar metacarpal region 106.

The plurality of sensing regions 122 of the sensor arrays 120 located along the hypothenar region 110 and the thenar region 112 are sized and shaped relative to the curvature and size of the hypothenar region 110 and the thenar region 112, respectively. Accordingly, the plurality of sensing regions 122 of the sensor arrays 120 located along the hypothenar region 110 and the thenar region 112 are relatively large and elongated due to a corresponding contour of the hypothenar region 110 and the thenar region 112. It should be understood that the plurality of sensing regions 122 within an individual sensor array 120 may vary in size and geometry relative one another. It should further be understood that various other sizes, geometries and positions of the one or more sensor arrays 120, and in particular the sensing regions 122 positioned therein, along the palmar surface region 104 may be included on the glove system 100 than those shown and depicted herein. As will be described in greater detail herein, with the glove system 100 including a plurality of sensing regions 122 within the one or more sensor arrays 120, the glove system 100 is configured to sense force loads applied thereto along general, non-discrete anatomical portions of an operator's hand (i.e., along the sensing regions 122). It should be understood that with the inclusion of the plurality of sensing regions 122 within the one or more sensor arrays 120, the glove system 100 may provide a general indication of a location along the glove system 100 where a pressure is received. As will be described in greater detail herein, inclusion of individual, discrete sensors may provide a specific indication of the location in which the glove system receives a pressure.

Figure 2:
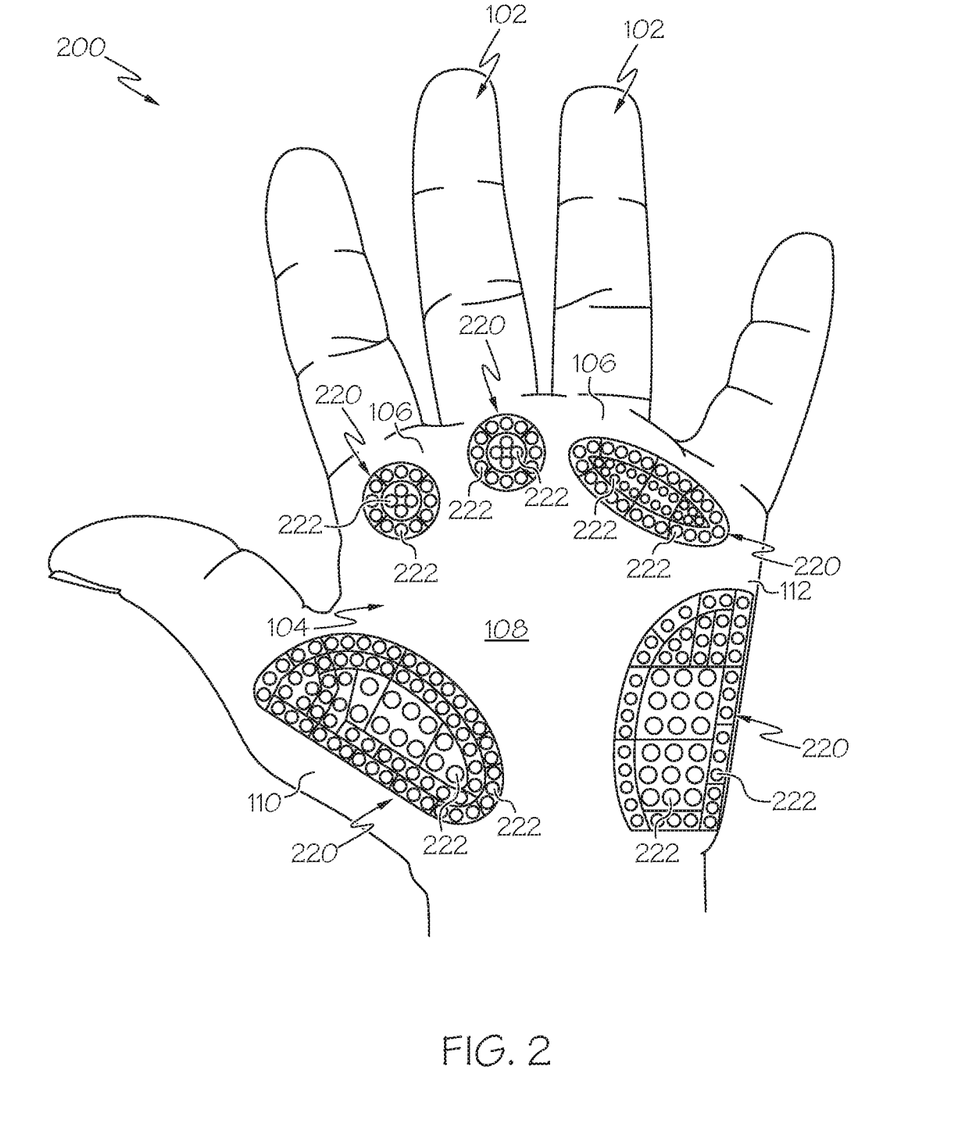
FIG. 2 schematically depicts another illustrative sensing glove system including a plurality of sensors along palmar surfaces of a glove according to one or more embodiments shown and described herein.

Referring now to FIG. 2, another illustrative glove system 200 is depicted. Except as otherwise described below, it should be understood that the glove system 200 is substantially similar to the glove system 100 described above such that like reference numerals are used to identify like components. However, the glove system 200 is different than the glove system 100 in that the glove system 200 includes a plurality of sensors 222 within the one or more sensor arrays 220 along the palmar surface region 104. In the present example, the palmar surface region 104 includes three sensor arrays 220 positioned along the palmar metacarpal region 106, one sensor array 220 positioned along the hypothenar region 110 and one sensor array 220 positioned along the thenar region 112. Each of the sensor arrays 220 of the glove system 200 include a plurality of individual, discrete sensors 222 positioned therein. The one or more sensor arrays 220 may be secured to and attached to the glove system 200 by various methods, including, but not limited to, printing the one or more sensor arrays 220 onto a fabric of the glove system 200, weaving the one or more sensor arrays 220 into a fabric of the glove system 200, adhesively securing the one or more sensor arrays 220 to the glove, and/or the like. It should be understood that additional and/or fewer sensor arrays 220 and/or sensors 222 may be positioned along various anatomical regions of the palmar surface region 104 than those shown and depicted herein without departing from the scope of the present disclosure.

In some embodiments, the plurality of sensors 222 of each of the one or more sensor arrays 220 are sized, shaped and positioned along the palmar surface region 104 relative to an intended-task to be performed with the glove system 200. In other words, a location and profile of the one or more sensor arrays 220, and the plurality of sensors 222 included therein, along the palmar surface region 104 of the glove system 200 may be determined based on a predetermined use of the glove system 200. Accordingly, the one or more sensor arrays 220 are sized and positioned along the corresponding regions 106, 108, 110, 112 of the palmar surface region 104 that generally receive a force load thereon when performing the predetermined task with an operator's hand. As will be described in greater detail herein, the one or more sensor arrays 220, and in particular the plurality of sensors 222, may be positioned along the finger surface region 102 of the glove system 200 for instances where an operator's hand generally receives a force load thereon when performing a predetermined task.

Still referring to FIG. 2, the plurality of sensors 222 of each of the one or more sensor arrays 220 are further sized, shaped and positioned along the palmar surface region 104 relative to a surface curvature of an operator's hand. In other words, a profile of the one or more sensor arrays 220, and the plurality of sensors 222 included therein, along the palmar surface region 104 of the glove system 200 may be determined based on a surface curvature of an operator's hand along the particular region 106, 108, 110, 112 of the palmar surface region 104 where the sensor array 220 is located. In the present example, the plurality of sensors 222 of the sensor arrays 220 located along the palmar metacarpal region 106 are sized and shaped relative to the curvature and size of the palmar metacarpal region 106. Accordingly, the plurality of sensors 222 of the sensor arrays 220 located along the palmar metacarpal region 106 are relatively small due to a corresponding contour of the palmar metacarpal region 106.

The plurality of sensors 222 of the sensor arrays 220 located along the hypothenar region 110 and the thenar region 112 are sized and shaped relative to the curvature and size of the hypothenar region 110 and the thenar region 112, respectively. Accordingly, the plurality of sensors 222 of the sensor arrays 220 located along the hypothenar region 110 and the thenar region 112 are relatively larger due to a corresponding contour of the hypothenar region 110 and the thenar region 112. It should be understood that the plurality of sensors 222 within an individual sensor array 220 may vary in size and shape relative one another. It should be further understood that various other sizes, shapes and positions of the one or more sensor arrays 220, and in particular the sensors 222 positioned therein, along the palmar surface region 104 may be included on the glove system 200 than those shown and depicted herein. As will be described in greater detail herein, with the glove system 200 including a plurality of sensors 222 within the one or more sensor arrays 220, the glove system 200 is configured to sense force loads applied thereto along particular, discrete anatomical portions of an operator's hand (i.e., on the sensors 222). It should be understood that with the inclusion of the plurality of individual, discrete sensors 222 within the one or more sensor arrays 220, the glove system 200 may provide a specific indication of a location along the glove system 200 where a pressure is received.

Figure 3A:
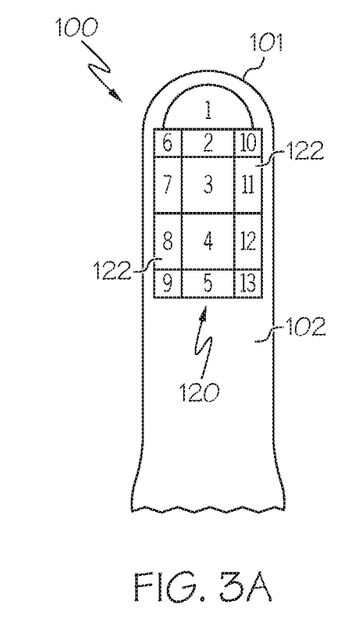
FIG. 3A schematically depicts the sensing glove system of FIG. 1 including a plurality of sensor regions extending along a finger surface of a glove according to one or more embodiments shown and described herein.

Referring now to FIG. 3A, the glove system 100 may further include one or more sensor arrays 120 positioned along one or more finger surface regions 102. The one or more sensor arrays 120 include a plurality of sensing regions 122 positioned therein that are relatively sized and shaped in correspondence to a predetermined use of the glove system 100 and/or a surface curvature of the finger surface region 102. For example, the plurality of sensing regions 122 of the sensor array 120 may extend up to and along a distal end 101 of the finger surface region 102 when the distal end 101 generally receives force loads thereon when performing a predetermined task with an operator's hand. Additionally or alternatively, by way of further example, the plurality of sensing regions 122 of the sensor array 120 may be curved along the finger surface region 102 in correspondence to a surface contour of an operator's hand at the finger surface region 102.

Figure 3B:
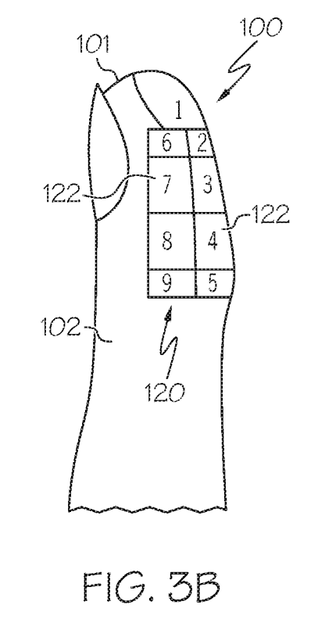
FIG. 3B schematically depicts the sensing glove system of FIG. 1 including the plurality of sensor regions extending along curved surfaces of the finger according to one or more embodiments shown and described herein.

Referring to FIG. 3B, in the present example the plurality of sensing regions 122 extend along curved anatomical portions of the finger surface region 102, in addition to planar anatomical portions, to thereby position at least one sensing region 122 of the sensor array 120 along each anatomical portion of the finger surface region 102 that generally receives a force load. The sensing regions 122 of the sensor array 120 positioned along the curved portions of the finger surface region 102 (e.g., anatomical portions 1, 6, 7, 8, 9, 10, 11, 12, and 13) are form-fitted to the curvature of the anatomical shape of an operator's finger. As described in greater detail herein, a material composition of the one or more sensor arrays 120 along the finger surface region 102 may vary relative to the one or more sensor arrays 120 positioned along the palmar surface region 104 to retain adequate finger tactility for the glove system 100, 200 along the finger surface regions 102. In particular, materials providing a reduced rigidity for the sensor arrays 120 along the finger surface regions 102 to thereby preserve ease of movement of the finger surface regions 102 by an operator of the glove system 100, 200. Additionally, a material thickness of the one or more sensor arrays 120 along the finger surface region 102 may vary relative to the one or more sensor arrays 120 positioned along the palmar surface region 104 to provide sufficient maneuverability for the glove system 100, 200 along the finger surface regions 102.

Although a single sensor array 120 is shown and described on the finger surface region 102 of the present example, it should be understood that additional and/or fewer sensor arrays 120 may be positioned along various other anatomical portions of the finger surface region 102 without departing from the scope of the present disclosure. Further, it should be understood that the plurality of sensing regions 122 within an individual sensor array 120 may vary in size and shape relative one another and various other sizes, shapes and positions of the one or more sensor arrays 120 and sensing regions 122 along the finger surface region 102 may be included on the glove system 100 than those shown and depicted herein.

Figure 4A:
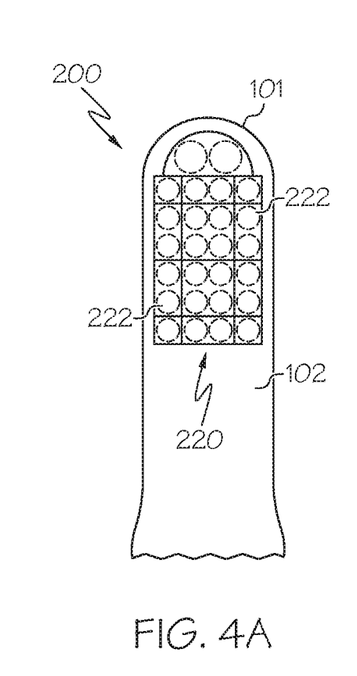
FIG. 4A schematically depicts the sensing glove system of FIG. 2 including a plurality of sensors extending along finger surfaces of a glove according to one or more embodiments shown and described herein.

Referring now to FIG. 4A, the glove system 200 may further include one or more sensor arrays 220 positioned along one or more finger surface regions 102. The one or more sensor arrays 220 include a plurality of sensors 222 positioned therein that are relatively sized and shaped in correspondence to a predetermined use of the glove system 200 and/or a surface curvature of the finger surface region 102. For example, the plurality of sensors 222 of the sensor array 220 may extend up to and along the distal end 101 of the finger surface region 102 when the distal end 101 generally receives force loads thereon when performing a predetermined task with an operator's hand. Additionally or alternatively, by way of further example, the plurality of sensors 222 of the sensor array 220 may be curved along the finger surface region 102 in correspondence to a surface contour of an operator's hand at the finger surface region 102.

Figure 4B:
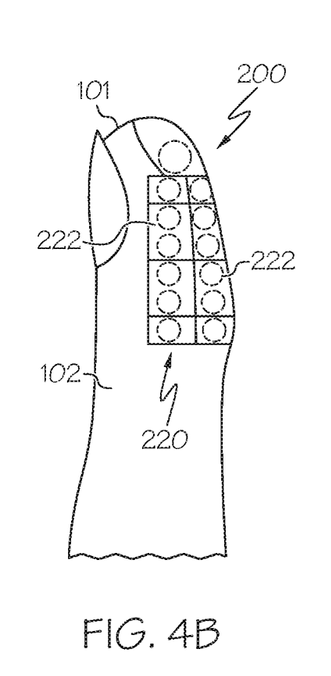
FIG. 4B schematically depicts the sensing glove system of FIG. 2 including the plurality of sensors extending along curved surfaces of the finger according to one or more embodiments shown and described herein.

Referring to FIG. 4B, in the present example the plurality of sensors 222 extend along curved anatomical portions of the finger surface region 102, in addition to planar anatomical portions, to thereby position at least one sensor 222 of the sensor array 220 along each anatomical portion of the finger surface region 102 that generally receives a force load. Although a single sensor array 220 is shown and described on the finger surface region 102 of the present example, it should be understood that additional and/or fewer sensor arrays 220 may be positioned along various other anatomical portions of the finger surface region 102 without departing from the scope of the present disclosure. Further, it should be understood that the plurality of sensors 222 within an individual sensor array 220 may vary in size and shape relative one another and various other sizes, shapes and positions of the one or more sensor arrays 220 and sensors 222 along the finger surface region 102 may be included on the glove system 200 than those shown and depicted herein.

Figure 5:
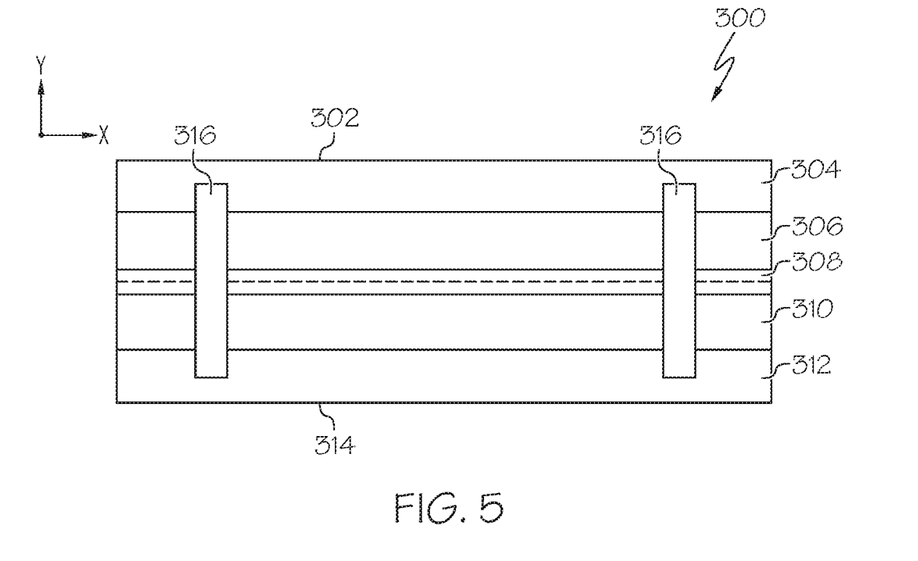
FIG. 5 schematically depicts an illustrative stack design of the sensors of the sensing glove system of FIGS. 1 and 2 according to one or more embodiments shown and described herein.

Referring now to FIG. 5, an illustrative transducer 300 of the sensing regions 122 and/or the sensors 222 are depicted. In particular, FIG. 5 shows a cross-sectional schematic of the sensing region 122 of the glove system 100 and/or the sensor 222 of the glove system 200 including the transducer 300. Accordingly, it should be understood that the sensing region 122 of the glove system 100 and/or the sensor 222 of the glove system 200 described above may comprise the transducer 300 shown herein. The transducer 300 may comprise a plurality of layers disposed over one another and is generally configured to maintain a thin normalization structure, such that the glove system 100, 200 is relatively lightweight when received along an operator's hand. The plurality of layers of the transducer 300 may include varying thicknesses, material compositions, and elasticity dependent on surface characteristics of an operator's hand in which the sensing region 122 and/or the sensor 222 is positioned along. It should be understood that although the plurality of layers of the transducer 300 is depicted as having a planar (i.e., flat) profile, dependent on an anatomical location of the sensing region 122 and/or the sensor 222 along the finger surface region 102 or palmar surface region 104 of the glove system 100, 200 the layers of the transducer 300 may be curved, angled, of varying thicknesses, and/or the like.

In the present example, the transducer 300 includes a sensing layer 308 positioned between an outer-diffusion layer 306 and an inner-diffusion layer 310 such that the sensing layer 308 is disposed therein. The transducer 300 further includes the outer-diffusion layer 306 and the inner-diffusion layer 310 positioned between an outer-contact layer 304 and an inner-contact layer 312 such that the pair of diffusion layers 306, 310 are disposed within the pair of contact layers 304, 312. In this instance, the outer-contact layer 304 and the inner-contact layer 312 define the external boundaries of the transducer 300 such that the remaining layers 306, 308, 310 are positioned therebetween. The outer-contact layer 304 defines an outer surface 302 opposite of the layers 306, 308, 310 and the inner-contact layer 312 defines an inner surface 314 opposite of the layers 306, 308, 310. It should be understood that the outer surface 302 of the transducer 300 is positioned relatively upward along the finger surface region 102 and/or the palmar surface region 104 such that the outer surface 302 faces opposite of, and is offset from, an operator's hand when received within the glove system 100, 200. Accordingly, the inner surface 314 of the transducer 300 is positioned relatively inward along the finger surface region 102 and/or the palmar surface region 104 such that the inner surface 314 faces toward, and abuts against, an operator's hand when received within the glove system 100, 200.

Still referring to FIG. 5, the transducer 300 further includes one or more guide features 316 extending through and connecting the plurality of layers 304, 306, 308, 310, 312. In the present example, the transducer 300 includes a pair of guide features 316 positioned perpendicularly relative to a direction in which the pair of contact layers 304, 312, the pair of diffusion layers 306, 310, and the sensing layer 308 extend. The pair of guide features 316 include a thickness that is relatively less than the pair of contact layers 304, 312 and the pair of diffusion layers 306, 310 such that the pair of guide features 316 are relatively soft and flexible. In some embodiments, the pair of guide features 316 comprises VeroWhitePlus™ photopolymers, three-dimensional printing material, digital materials, and/or the like. The pair of guide features 316 is configured to maintain an alignment of the pair of contact layers 304, 312, the pair of diffusion layers 306, 310, and the sensing layer 308 to thereby improve a detection accuracy of a force received along the sensing region 122 and/or the sensor 222. The pair of guide features 316 may further reduce a longitudinal loading on the sensing layer 308. As will be described in greater detail herein, the transducer 300 of the sensing region 122 and/or the sensor 222 may include additional and/or fewer layers and/or guide features than those shown and described herein without departing from the scope of the present disclosure.

For example, a quantity of the guide features 316 included in the transducer 300 of the sensing region 122 and/or the sensor 222 may be dependent on a shape and/or contour of the anatomical region of an operator's hand in which the sensing region 122 and/or the sensor 222 is to be positioned along. In instances where the sensing region 122 and/or the sensor 222 is positioned along an anatomical region of an operator's hand that includes a substantial curvature (e.g., the distal end 101 of the finger surface region 102, the thenar region 112, and the like), additional guide features 316 may be required to maintain adequate alignment of the plurality of layers 304, 306, 308, 310, 312 of the transducer 300. In contrast, fewer and/or no guide features 316 may be required when the sensing region 122 and/or the sensor 222 is positioned along an anatomical region of an operator's hand that does not include a substantial shape or contour (e.g., the palmar metacarpal region 106, the median palmar region 108, the hypothenar region 110, and the like).

Referring still to FIG. 5, a lateral distance between the one or more guide features 316 may increase and/or decrease dependent on a shape and/or contour of the anatomical region of an operator's hand in which the sensing region 122 and/or the sensor 222 is to be positioned along. In instances where the sensing region 122 and/or the sensor 222 is positioned along an anatomical region of an operator's hand that includes a substantial curvature (e.g., the distal end 101 of the finger surface region 102, the thenar region 112, and the like), a smaller lateral distance between the two or more guide features 316 may be required to maintain adequate alignment of the plurality of layers 304, 306, 308, 310, 312 of the transducer 300 as compared to an anatomical region of the operator's hand that has less curvature (e.g., the palmar metacarpal region 106, the middle palmar region 108, the hypothenar region 110, and the like). In contrast, a greater lateral distance may be adequate between the two or more guide features 316 when the sensing region 122 and/or the sensor 222 is positioned along an anatomical region of an operator's hand that does not include a substantial shape or contour (e.g., the palmar metacarpal region 106, the middle palmar region 108, the hypothenar region 110, and the like) as compared to an anatomical region of the operator's hand that has more curvature (e.g., the distal end 101 of the finger surface region 102, the thenar region 112, and the like).

The sensing layer 308 of the transducer 300 is a pressure sensor that includes a three-dimensional load cell configured to convert a pressure (e.g., force load) received thereon into an electrical signal indicative of a magnitude of the pressure applied thereto. In some embodiments, the sensing layer 308 is a printed layer comprising, for example, a piezoresistive fabric, a polyethylene terephthalate (PET), and the like. The sensing layer 308 is a flexible layer relative to the pair of contact layers 304, 312 and the pair of diffusion layers 306, 310 due to a relatively smaller thickness, material composition, and/or the like. In some embodiments the sensing layer 308 may include one or more intermediate layers disposed about the sensing layer 308 such that the sensing layer 308 is separated by the pair of diffusion layers 306, 310 by the one or more intermediate layers. The intermediate layer may comprise a coating, film, fabric, conductive ink, polymer, hard plastic, and/or the like. In other embodiments, the transducer 300 may include a sensor pocket for receiving the sensing layer 308 therein and between the pair of diffusion layers 306, 310 and the pair of contact layers 304, 312 such that the sensing layer 308 may be selectively removed and replaced when necessary.

Still referring to FIG. 5, the pair of diffusion layers 306, 310 and the pair of contact layers 304, 312 are formed of three-dimensional printed digital material having an elasticity. In some embodiments, the pair of contact layers 304, 312 and/or the pair of diffusion layers 306, 310 may comprise VeroWhitePlus™, Tank Black Plus™, and/or the like. Generally, the outer-contact layer 304 and the outer-diffusion layer 306 include material compositions that provide incompressible, rigid characteristics relative to the inner-contact layer 312 and the inner-diffusion layer 310, which include material compositions that provide compressible, softer characteristics. In some embodiments, the pair of diffusion layers 306, 310 includes a greater elasticity than the pair of contact layers 304, 312 such that the pair of diffusion layers 306, 310 are flexible relative to the pair of contact layers 304, 312. In this instance, the pair of contact layers 304, 312 provides a rigid, outer composition for the transducer 300 of the sensing region 122 and/or the sensor 222. As will be described in greater detail herein, the enhanced elasticity of the pair of diffusion layers 306, 310 allows the pair of diffusion layers 306, 310 to selectively compress and/or deform when a load (i.e., force) is received on the sensing region 122 and/or the sensor 222 to redirect the load toward the sensing layer 308 disposed therebetween.

For example, the pair of diffusion layers 306, 310 may include an elasticity that ranges from a Shore Hardness value of about 27 A to about 50 A, and the pair of contact layers 304, 312 may include an elasticity that ranges from a Shore Hardness value of about 70 A to 95 A in some embodiments, from 15D to 50D in some embodiments, and about 95 A to about 80D in some embodiments. It should be understood that in instances where the sensor array 220 of the glove system 200 includes a plurality of sensors 222 positioned therein (See, e.g., FIGS. 4A-4B), the pair of contact layers 304, 312 and/or the pair of diffusion layers 306, 310 of the plurality of sensors 222 may include a relatively softer material having a lower Shore Hardness value to further enhance a tactility of the individual, discrete sensors 222 of the transducer 300. For example, the pair of contact layers 304, 312 of the plurality of sensors 222 may comprise a material having an elasticity with a Shore Hardness value of about 65 A to about 70 A (which may correspond to a Shore Hardness of 15D in some embodiments), and more particularly about 60 A to about 70 A (which may correspond to a Shore Hardness of 15D in some embodiments). By way of further example, the pair of diffusion layers 306, 310 of the plurality of sensors 222 may comprise a material having an elasticity with a Shore Hardness value of about 27 A to 35 A.

Alternatively, in instances where the sensing region 122 and/or the sensor 222 of the glove system 100, 200 is positioned along an anatomical portion of an operator's hand that includes a surface curvature that requires the layers of the transducer 300 to be form-fitted, one or more layers of the transducer 300 may include a material having a greater Shore Hardness value to provide adequate rigidity to the sensing region 122 and/or the sensor 222. For example, with the glove system 100 including one or more sensor arrays 120 having a plurality of sensing regions 122 (See, e.g., FIGS. 1, 3A-3B), the outer-contact layer 304 of the sensing region 122 may include a Shore Hardness value of about 95 A to about 100 A in some embodiments, from about 50D to about 60D in some embodiments, and the inner-contact layer 312 of the sensing region 122 may include a Shore Hardness value of about 70 A to about 80 A in some embodiments, or from about 15D to about 30D in some embodiments. Further, with the glove system 200 including one or more sensor arrays 220 having a plurality of sensors 222 (FIGS. 2, 4A-4B), the outer-contact layer 304 of the sensor 222 may include a Shore Hardness value of about 80 A to about 95 A in some embodiments, or about 30D to about 50D in some embodiments, and the inner-contact layer 312 of the of the sensor 222 may include a Shore Hardness value of about 60 A to about 75 A (which may correspond to about, 20D in some embodiments). It should be understood that the pair of contact layers 304, 312 of the sensing region 122 of the glove system 100 (See, e.g., FIGS. 1, 3A-3B) include a relatively harder material composition than the pair of contact layers 304, 312 of the glove system 200 (See, e.g., FIGS. 2, 4A-4B) as a localization area of an individual, discrete sensor 222 may be relatively smaller than an area of a sensing region 122 such that an increased hardness is required to maintain proper strength for the transducer 300 of the plurality of sensing regions 122 due to a greater size (e.g., surface area) of the transducer 300.

Referring still to FIG. 5, in some embodiments an elasticity of the inner-diffusion layer 310 and/or the inner-contact layer 312 may differ from the outer-diffusion layer 306 and the outer-contact layer 304, respectively, in instances where the transducer 300 of the sensing region 122 and/or the sensor 222 is located along an anatomical portion of an operator's hand where enhanced tactility and maneuverability is desirable, such as, for example, the finger surface regions 102, the thenar region 112, and the like of the glove system 100, 200. In particular, the inner-diffusion layer 310 may include a Shore Hardness that differs from a Shore Hardness of the outer-diffusion layer 306 to provide adequate tactility for an operator's hand received within the glove system 100, 200, since the inner-diffusion layer 310 is positioned relatively adjacent to the inner surface 314 of the transducer 300 which may abut against an operator's hand. For example, the inner-diffusion layer 310 may include an elasticity that ranges from a Shore Hardness value of about 27 A to about 35 A. In other embodiments the inner-contact layer 312 may include a Shore Hardness that differs from a Shore Hardness of the outer-contact layer 304 to provide enhanced maneuverability for an operator's hand received within the glove system 100, 200, since the inner-contact layer 312 is positioned relatively adjacent to the inner surface 314 of the transducer 300 which may abut against an operator's hand. For example, the inner-contact layer 312 may include an elasticity that ranges from a Shore Hardness value of about 60 A to about 70 A (which may correspond to a Shore Hardness value of about 15D in some embodiments).

The pair of diffusion layers 306, 310 of the transducer 300 includes a greater thickness than the pair of contact layers 304, 312. For example, the pair of diffusion layers 306, 310 may include a thickness of about 0.25 millimeters to about 0.5 millimeters and the pair of contact layers 304, 312 may include a thickness of about 0.1 millimeters to about 0.2 millimeters. It should be understood that in instances where the sensor array 220 of the glove system 200 includes a plurality of sensors 222 positioned therein (See, e.g., FIGS. 4A-4B), the pair of contact layers 304, 312 and/or the pair of diffusion layers 306, 310 may include a relatively thinner material having a smaller thickness to further enhance a tactility of the individual, discrete sensors 222 of the transducer 300. For example, the pair of contact layers 304, 312 of the plurality of sensors 222 may comprise a material having a thickness of about 0.15 millimeters to about 0.2 millimeters. By way of further example, the pair of diffusion layers 306, 310 of the plurality of sensors 222 may comprise a material having a thickness of about 0.3 millimeters to about 0.5 millimeters, and more particularly 0.15 millimeters to about 0.2 millimeters.

Alternatively, in instances where the sensing region 122 and/or the sensor 222 of the glove system 100, 200 is positioned along an anatomical portion of an operator's hand that includes a surface curvature that requires the layers of the transducer 300 to be form-fitted, one or more layers of the transducer 300 may include a material having a thinner thickness to provide adequate rigidity to the sensing region 122 and/or the sensor 222. For example, with the glove system 100, 200 including one or more sensor arrays 120, 220 having a plurality of sensing regions 122 and/or sensors 222 (See, e.g., FIGS. 1-4), the inner-diffusion layer 310 may include a thickness of about 0.15 millimeters to about 0.20 millimeters. It should be understood that the inner-diffusion layer 310 of the sensing region 122 of the glove system 100 (See, e.g., FIGS. 1, 3A-3B) and the inner-diffusion layer 310 of the glove system 200 (See, e.g., FIGS. 2, 4A-4B) may include similar thicknesses in instances where the anatomical portion that the sensing region 122 and/or the sensor 222 is located includes a substantial surface curvature as adequate force diffusion across the inner-diffusion layer 310 requires a minimum material thickness. However, it should be understood that a thickness of the inner-diffusion layer 310, and/or the other layers of the transducer 300, may vary dependent on a compressibility of an operator's hand along the anatomical portion where the sensing region 122 and/or the sensor 222 of the glove system 100, 200 is located, such that the thickness and elasticities described herein may vary per operator.

Referring still to FIG. 5 and as described above, in some embodiments an elasticity of the inner-diffusion layer 310 and/or the inner-contact layer 312 may differ from the outer-diffusion layer 306 and the outer-contact layer 304, respectively, in instances where the transducer 300 of the sensing region 122 and/or the sensor 222 is located along an anatomical portion of an operator's hand where enhanced tactility and maneuverability is desirable, such as, for example, the finger surface regions 102, the thenar region 112, and the like of the glove system 100, 200. In particular, the inner-diffusion layer 310 may include a thickness that differs from a thickness of the outer-diffusion layer 306 to provide adequate tactility for an operator's hand received within the glove system 100, 200, since the inner-diffusion layer 310 is positioned relatively adjacent to the inner surface 314 of the transducer 300 which may abut against an operator's hand. For example, the inner-diffusion layer 310 may include a thickness that ranges from about 0.25 millimeters to about 0.35 millimeters, and more particularly 0.15 millimeters to about 0.20 millimeters. In other embodiments the inner-contact layer 312 may include a thickness that differs from a thickness of the outer-contact layer 304 to provide enhanced maneuverability for an operator's hand since the inner-contact layer 312 is positioned adjacent to the inner surface 314 of the transducer 300, relative to the outer-contact layer 304. For example, the inner-contact layer 312 may include a thickness that ranges from about 0.10 millimeters to about 0.20 millimeters.

It should be understood that in some embodiments one or more layers of the transducer 300 may be modified or omitted based on a physiology of an operator's hand that is to be received within the glove system 100, 200, a task to be performed by the glove system 100, 200, and/or the like. Alternatively, in instances where the glove system 200 includes one or more sensor arrays 220 that have a plurality of sensors 222 positioned therein, one or more layers of the transducer 300 of the plurality of sensors 222 may be modified or omitted to increase a capability of the glove system 200 to detect a specific location in which a pressure is applied to the glove system 200. For example, in embodiments where the sensor array 120, 220 of the glove system 100, 200 may be positioned along portions of the palmar surface region 104 that include an inherently rigid surface (e.g., the palmar metacarpal region 106, the middle palmar region 108, and the like), a thickness of one or more layers of the transducer 300 may be reduced, an elasticity of one or more layers of the transducer 300 may be increased, and/or one or more layers of the transducer 300 may be omitted. In other words, due to the naturally rigid surface characteristics of certain anatomical portions of an operator's hand, the transducer 300 of the sensing regions 122 and/or sensors 222 may not be required to include a rigid configuration.

By way of further example, in embodiments where the sensor array 120, 220 of the glove system 100, 200 may be positioned along portions of the palmar surface region 104 that include an inherently flexible surface (e.g., the hypothenar region 110, the thenar region 112, and the like), a thickness of one or more layers of the transducer 300 may be increased, an elasticity of one or more layers of the transducer 300 may be reduced, and/or one or more layers of the transducer 300 may be omitted. In other words, due to the naturally soft surface characteristics of certain anatomical portions of an operator's hand, the transducer 300 of the sensing regions 122 and/or sensors 222 may be required to include a rigid configuration.

Still referring to FIG. 5, the inner-diffusion layer 310 and/or the inner-contact layer 312 may be omitted entirely from the transducer 300, such as, for example, in instances where the sensor array 220 of the glove system 200 includes a plurality of sensors 222 therein. In this instance, one or more of the plurality of sensors 222 may include the transducer 300 comprising at least the outer-contact layer 304, the outer-diffusion layer 306, and the sensing layer 308. In this embodiment, with an omission of one or more of the inner-diffusion layer 310 and/or the inner-contact layer 312, a thickness and/or material elasticity of the remaining layers of the transducer 300 may be varied to accommodate for the omission. For example, omitting the inner-contact layer 312 of the transducer 300 may be accommodated by increasing a thickness of the inner-diffusion layer 310 to provide suitable rigidity for the transducer 300 to perform adequate force distribution (e.g., ranging from about 0.25 millimeters to about 0.35 millimeters). Additionally, a material elasticity of the inner-diffusion layer 310 of the transducer 300 may be decreased to provide adequate diffusion of pressure across the sensing region due to an omission of the inner-contact layer 312 (e.g., ranging from a Shore Hardnes of about 50 A to about 60 A). In other words, a hardness and/or rigidity of the inner-diffusion layer 310 of the transducer 300 may be increased to accommodate for the omission of the inner-contact layer 312 to adequately receive, distribute, and normalize the force load received along the inner surface 314 of the transducer 300 through such the inner-diffusion layer 310.

In other embodiments the outer-contact layer 304 and the outer-diffusion layer 306 may be omitted for a single outer layer (not shown) disposed over the sensing layer 308. In this embodiment, the material compositions of the outer-contact layer 304 and the outer-diffusion layer 306 may be collectively provided in a single outer layer to adequately provide the rigidity, compressibility, and structure collectively provided in the outer-contact layer 304 and the outer-diffusion layer 306. In this instance, only a single layer is printed atop the sensing layer 308 such that the single outer layer is configured and operable to perform the distribution and diffusion characteristics originally performed by the outer-contact layer 304 and the outer-diffusion layer 306 described herein, respectively. The single outer layer may include an elasticity ranging from a Shore Hardness of about 27 A to about 95 A. In particular, the single outer layer may include a varying elasticity (i.e., Shore Hardness) through a lateral thickness of the layer to thereby facilitate a both distribution and diffusion of a force therethrough. In other words, the single outer layer of the present embodiment is configured to receive a force, distribute the force into a plurality of forces, and normalize the plurality of forces prior to conveying the plurality of normalized-forces to the sensing layer 308 secured thereto.

It should be understood that the inner-contact layer 312 and the inner-diffusion layer 310 may similarly be omitted for a single inner layer (not shown) disposed over the sensing layer 308, in lieu of the single outer layer and/or in addition to the single outer layer. In particular, the single inner layer may be disposed over the sensing layer 308 along a surface opposite of the single outer layer. A material composition of the inner-contact layer 312 and the inner-diffusion layer 310 may be collectively provided in a single inner layer to adequately provide the rigidity, compressibility, and structure collectively provided in the inner-contact layer 312 and the inner-diffusion layer 310. In this instance, only a single layer is printed along the sensing layer 308, opposite a surface of the sensing layer 308 including the single outer layer, such that the single inner layer is configured and operable to perform the distribution and diffusion characteristics originally performed by the inner-contact layer 312 and the inner-diffusion layer 310 described herein, respectively. The single inner layer may include a varying elasticity (i.e., Shore Hardness) through a lateral thickness of the layer to thereby facilitate a distribution and diffusion of forces therethrough. In other words, the single inner layer of the present embodiment is configured to receive a force (e.g., normal force), distribute the force into a plurality of forces, and normalize the plurality of forces prior to conveying the plurality of normalized-forces to the sensing layer 308 secured thereto.

Figure 6:
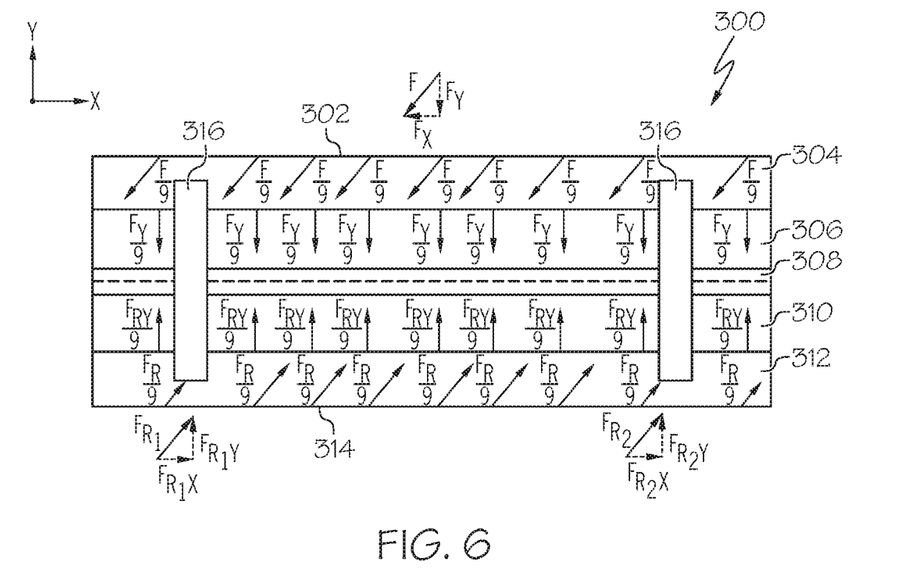
FIG. 6 schematically depicts illustrative force distribution across the stack design of the sensors of sensing glove system of FIGS. 1 and 2 according to one or more embodiments shown and described herein.
Figure 7:
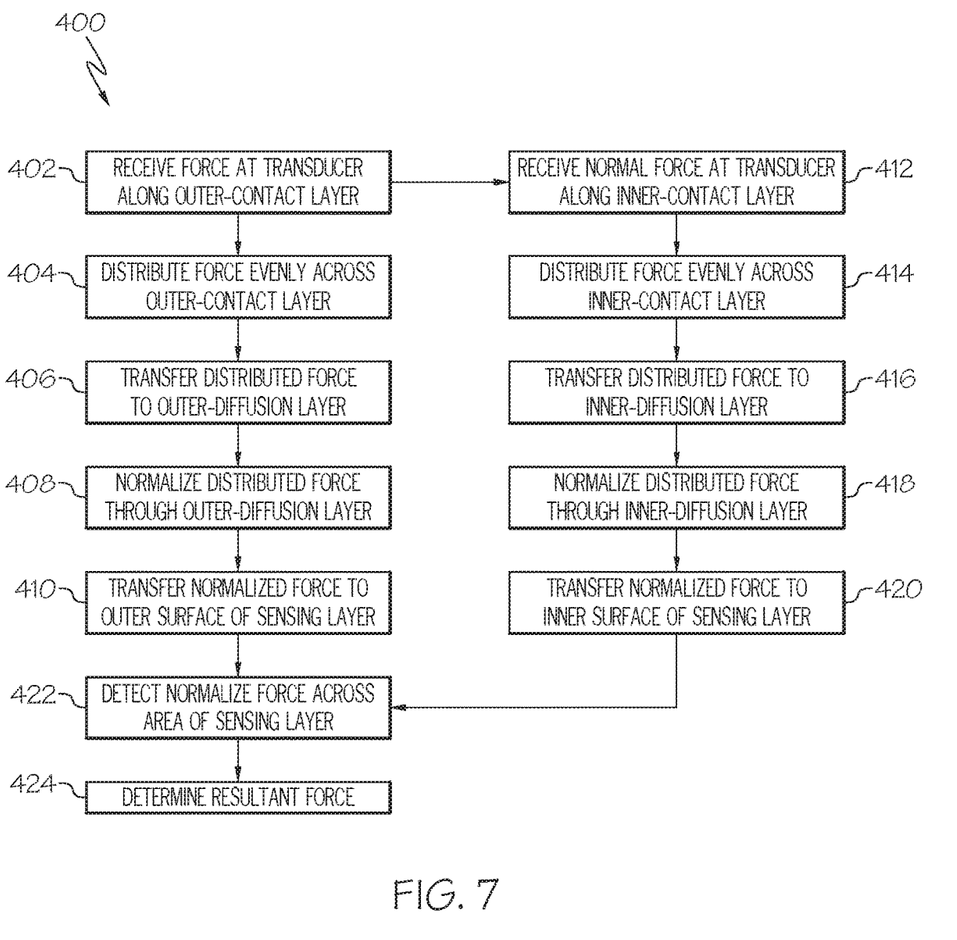
FIG. 7 depicts a flow diagram of an illustrative method of distributing a force across a sensor of the sensing glove system of FIGS. 1 and 2 according to one or more embodiments shown and described herein.

Referring now to FIG. 6 in conjunction with the flow diagram of FIG. 7, an exemplary method 400 of detecting and measuring a force load applied to the glove system 100, 200 is schematically depicted. More specifically, the glove system 100, 200 is operable to measure a resultant pressure generated from force loads received along the one or more sensor arrays 120, 220 of the glove system 100, 200 at various angular orientations relative to the planar surface of an occupant's hand. The depiction of FIGS. 6-7 and accompanying description below is not meant to limit the subject matter described herein or represent an exact description of how forces may be distributed among the layers, but instead is meant to provide a simple schematic overview to illustrate the general force distribution characteristics of the layers described herein.

Referring to FIG. 6 and at step 402, a force F is received along at least one of the one or more sensor arrays 120, 220 of the glove system 100, 200 (FIGS. 1-2), and in particular along the outer-contact layer 304 of the transducer 300 of the sensing region 122 and/or the sensor 222. The force F consists of a horizontal component $F_X$ and a vertical component $F_Y$ such that the force vector F is received along the outer-contact layer 304 at a transverse orientation relative to the outer surface 302 of the transducer 300. In other words, the force F is a vector quantity that includes both a magnitude and direction received along the sensing region 122 and/or the sensor 222 of the glove system 100, 200. At step 412, in response to the outer-contact layer 304 receiving the force F along the outer surface 302 of the transducer 300, one or more normal forces $F_{R1}$, $F_{R2}$ are generated and received at the inner-contact layer 312 along the inner surface 314 of the transducer 300. The one or more normal forces $F_{R1}$, $F_{R2}$ are reactive forces applied to the transducer 300 by the operator's hand positioned adjacent to and abutting against the inner surface 314. The normal forces $F_{R1}$, $F_{R2}$ consists of a horizontal component $F_R{}^1{}_X$, $F_R{}^2{}_X$ and a vertical component $F_R{}^1{}_Y$, $F_R{}^2{}_Y$ such that the normal force vectors $F_{R1}$, $F_{R2}$ are received along the inner-contact layer 312 at a transverse orientation relative to the inner surface 314 of the transducer 300.

Accordingly, the sensing region 122 and/or the sensor 222 receives at least one force F at the outer-contact layer 304 by an external object engaging the glove system 100 and at least one normal force $F_R$ at the inner-contact layer 312 by an operator's hand positioned therein. It should be understood that the quantity of normal forces $F_R$ received along the inner-contact layer 312 may correspond to a number of contact points along the inner-contact layer 312 in which the transducer 300 engages an occupant's hand thereon when the force F is applied to the transducer 300. In the present example, the transducer 300 engages an occupant's hand along the inner surface 314 at two locations such that a pair of normal forces $F_{R1}$, $F_{R2}$ are generated and applied to the inner-contact layer 312. It should be understood that additional and/or fewer forces F and/or normal forces $F_{R1}$, $F_{R2}$ may be applied to the sensing region 122 and/or the sensor 222 of the glove system 100, 200 than those shown and depicted herein without departing from the scope of the present disclosure.

Still referring to FIG. 6 and at step 404, the outer-contact layer 304 distributes the force F received along the outer surface 302 of the transducer 300 evenly therethrough such that the force F is equally distributed through an area of the outer-contact layer 304. It should be understood that dependent on a magnitude of the force vector F, the force F is divided an "N" number of times $$\frac{F}{N}$$

such that the initial force F received at the transducer 300 is equally distributed through the outer-contact layer 304 and toward the outer-diffusion layer 306. In the present example, the force F is dispersed through the outer-contact layer 304 into nine equal distributions $$\frac{F}{9},$$

however, in other examples the force vector F may include a greater and/or lesser magnitude such that the force F may be dispersed into various other distribution amounts. At step 414, the inner-contact layer 312 distributes the normal forces $F_{R1}$, $F_{R2}$ received along the inner surface 314 of the transducer 300 evenly therethrough such that the normal forces $F_{R1}$, $F_{R2}$ (i.e., reactive forces) are equally distributed through an area of the inner-contact layer 312. It should be understood that dependent on a magnitude of the force vector F, the normal forces $F_{R1}$, $F_{R2}$ are divided an "N" number of times $$\frac{FR}{N}$$

such that the initial normal forces $F_{R1}$, $F_{R2}$ received at the transducer 300 are equally distributed through the inner-contact layer 312 and toward the inner-diffusion layer 310 at a substantially equivalent quantity as the initial force vector F along the outer-contact layer 304. In the present example, the normal forces $F_{R1}$, $F_{R2}$ are dispersed through the inner-contact layer 312 into nine equal distributions $$\frac{FR}{9}$$

in corresponaence to me aistributions of the force $$\frac{F}{9}$$

in the outer-contact layer 304.

At step 406, with the forces $$\frac{F}{9}$$

distributed across the area of the outer-contact layer 304 into one or more force segments, the distributed forces $$\frac{F}{9}$$

are transferred onto me outer-diffusion layer 306 that is positioned adjacent to and in communication with the outer-contact layer 304. In this instance, the outer-diffusion layer 306 receives the distributea forces $$\frac{F}{9}$$

across a surface area of the outer-diffusion layer 306 at various locations corresponding to the one or more segments distributed by the outer-contact layer 304. At step 408, the outer-diffusion layer 306 normalizes the distributed forces $$\frac{F}{9}$$

received from the outer-contact layer 304 therethrough such that the force vectors $$\frac{F}{9}$$

are stabilized and transitioned into scalar forces $$\frac{FY}{9}$$

with an accumulative magnitude equivalent to the magnitude of the force vector F initially received at the outer-contact layer 304. At step 416, with the normal forces $$\frac{FR}{9}$$

distrubuted across tne area of the inner-contact layer 312 into one or more normal force segments $$\frac{FR}{9},$$

the distributed normal forces $$\frac{FR}{9}$$

are transferred onto tne inner-diffusion layer 310 that is positioned adjacent to and in communication with the inner-contact layer 312. In this instance, the inner-diffusion layer 310 receives the distributed normal forces $$\frac{FR}{9}$$

across a surface area of tne inner-diffusion layer 310 at various locations corresponding to the one or more segments $$\frac{FR}{9}$$

distributed by the inner-contact layer 312. At step 418, the inner-diffusion layer 310 normalizes the distributea normal forces $$\frac{FR}{9}$$

received from the inner-contact layer 312 therethrough such that the normal force vectors $$\frac{FR}{9}$$

are stabilized and transitioned into scalar forces $$\frac{FRY}{9}$$

with an accumulative magnitude equivalent to the original magnitude of the normal force vectors $F_{R1}$, $F_{R2}$ received at the inner-contact layer 312.

Still referring to FIG. 6, at step 410 with the scalar forces $$\frac{FY}{9}$$

normalized and distributed across the area of the outer-diffusion layer 306, the normalized and distributed forces $$\frac{FY}{9}$$

are transferred onto the sensing layer 308 that is positioned adjacent to and in communication with the outer-diffusion layer 306. In this instance, the sensing layer 308 receives the normalized and distributed forces $$\frac{FY}{9}$$

across a surface area of the sensing layer 308 at various locations, along an outer surface of the sensing layer 308, corresponding to the one or more segments distributed by the outer-diffusion layer 306. At step 420, with the scalar normal forces $$\frac{FRY}{9}$$

normalized and distributed across the area of the inner-diffusion layer 310, the normalized and distributed normal forces $$\frac{FRY}{9}$$

are transferred onto me sensing layer 308 that is positioned adjacent to and in communication with the inner-diffusion layer 310. In this instance, the sensing layer 308 receives the normalized and distributed normal forces $$\frac{FRY}{9}$$

across a surface area of the sensing layer 308 at various locations, along an inner surface of the sensing layer 308, corresponding to the one or more segments distributed by the inner-diffusion layer 310.

At step 422, the sensing layer 308 receives and detects the normalized and distributed forces $$\frac{FY}{9}$$

from the outer layers 304, 306 (i.e., the outer-contact layer 304 and the outer-diffusion layer 306) and the normalized and distributed normal forces $$\frac{FRY}{9}$$

from the inner layers 310, 312 (i.e., the inner-diffusion layer 310 and the inner-contact layer 312) at a plurality of locations across a surface area of the sensing layer 308. In this instance, the plurality of forces are equally distributed and applied to the sensing layer 308 at scalar quantities that are measurable with greater accuracy due to the even distribution and normalized force vectors. At step 424, with a magnitude of the initial force F and the normal forces $F_{R1}$, $F_{R2}$ measured, the sensing layer 308 determines a resultant pressure applied to the sensing region 122 and/or the sensor 222 of the glove system 100, 200.

The above-described system includes a pressure sensing glove system that provides a plurality of sensor arrays positioned along various anatomical regions of the glove, with each sensor array including one or more non-discrete sensing regions and/or discrete sensors positioned therein for detecting and measuring a force applied thereto. The one or more non-discrete sensing regions and/or discrete sensors comprise a transducer that includes a sensor disposed within a pair of diffusion layers and further disposed within a pair of contact layers that distribute a force received along the outer surfaces of the transducer across the pair of diffusion layers. The pair of diffusion layers thereby normalize the forces received from the pair of contact layers and distribute the normalized forces across the sensing layer disposed therein for detection and to determine a resultant pressure applied to the sensor.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A pressure sensing device for measuring a force, comprising:
    a sensor including
        a pair of contact layers for receiving a force including a horizontal component and a vertical component;
        a pair of diffusion layers disposed between the pair of contact layers, wherein the pair of contact layers distribute a force received along outer surfaces of the sensor across the pair of diffusion layers; and
        a sensing layer disposed between the pair of diffusion layers, wherein the pair of diffusion layers normalize the force received from the pair of contact layers across the sensing layer such that the force is transitioned into a scalar force including the vertical component of the force,
    wherein the sensing layer receives the scalar force at a plurality of locations across a surface area of the sensing layer to determine a resultant pressure applied to the sensor,
    wherein the pair of contact layers includes an inner-contact layer and an outer-contact layer, the inner-contact layer having a greater elasticity than the outer-contact layer, and the pair of diffusion layers includes an inner-diffusion layer and an outer-diffusion layer, the inner-diffusion layer having a greater elasticity than the outer-diffusion layer.

2. The pressure sensing device of claim 1, wherein the sensor is a three-dimensional load cell printed along the pressure sensing device that converts a pressure acting on the sensor into an electrical signal.

3. The pressure sensing device of claim 2, wherein a magnitude of the electrical signal comprises a resultant amount of force received at the sensor.

4. The pressure sensing device of claim 1, wherein the pair of diffusion layers and the pair of contact layers are formed of three-dimensional printed digital material including an elasticity.

5. The pressure sensing glove device of claim 4, wherein the pair of diffusion layers includes a greater thickness than the pair of contact layers.

6. The pressure sensing device of claim 5, wherein the thickness of the pair of diffusion layers is about 0.5 millimeters and the thickness of the pair of contact layers is about 0.2 millimeters.

7. The pressure sensing device of claim 1, wherein the pair of diffusion layers include a greater elasticity than the pair of contact layers such that the pair of diffusion layers are flexible relative to the pair of contact layers.

8. The pressure sensing device of claim 7, wherein the elasticity of the pair of diffusion layers ranges from a Shore Hardness value of about 27 A to 50 A.

9. The pressure sensing device of claim 8, wherein the elasticity of the pair of contact layers ranges from a Shore Hardness value of about 75 A to 95 A.

10. The pressure sensing device of claim 1, wherein a first layer of the pair of contact layers extends along an outer surface of the pressure sensing device and a second layer of the pair of contact layers extends along an inner surface of the pressure sensing device.

11. The pressure sensing device of claim 10, wherein the first layer of the pair of contact layers receives the force from the outer surface of the pressure sensing device and the second layer of the pair of contact layers receives a normal force generated at the inner surface of the pressure sensing device in response to the first layer of the pair of contact layers receiving the force at the outer surface.

12. The pressure sensing device of claim 1, wherein the sensor further includes a guide feature extending perpendicularly through the pair of contact layers, the pair of diffusion layers, and the sensing layer.

13. The pressure sensing device of claim 12, wherein the guide feature maintains an alignment of the pair of contact layers, the pair of diffusion layers, and the sensing layer to thereby improve a detection accuracy of the force received at the sensor.

14. The pressure sensing device of claim 1, wherein:
the elasticity of the inner contact layer ranges from a Shore Hardness value of about 60 A to about 75 A;
the elasticity of the outer contact layer ranges from a Shore Hardness value of about 80 A to 95 A;
the elasticity of the inner diffusion layer ranges from a Shore Hardness value of about 27 A to 35 A; and
the elasticity of the outer diffusion layer ranges from a Shore Hardness value of about 27 A to 50 A.

15. A method comprising:
receiving a force applied to a device including a sensor at a location along an outer-contact layer and an inner-contact layer of the sensor, the force including a horizontal component and a vertical component;
distributing the force from the location along the outer-contact layer and the inner-contact layer to a plurality of locations across the outer-contact layer and the inner-contact layer;
receiving the forces from the plurality of locations of the outer-contact layer and the inner-contact layer at a plurality of locations of an outer-diffusion layer and an inner-diffusion layer of the sensor, wherein the outer-diffusion layer and the inner-diffusion layer are disposed beneath the outer-contact layer and the inner-contact layer relative to the force received thereon;
transitioning the force into a scalar force including the vertical component of the force to normalize the forces through the outer-diffusion layer and the inner-diffusion layer at the plurality of locations across the outer-diffusion layer and the inner-diffusion layer; and
receiving the forces across a surface area of a sensing layer of the sensor, wherein the sensing layer is disposed between the outer-diffusion layer and the inner-diffusion layer,
wherein the inner-contact layer has a greater elasticity than the outer-contact layer, and
wherein the inner-diffusion layer has greater elasticity than the outer-diffusion layer.

16. The method of claim 15, further comprising receiving a normal force at a location along an inner-contact layer of the sensor in response to the outer-contact layer of the sensor receiving the force.

17. The method of claim 16, further comprising distributing the normal force from the location along the inner-contact layer to a plurality of locations across the inner-contact layer, and receiving the normal forces from the plurality of locations of the inner-contact layer at a plurality of locations of an inner-diffusion layer of the sensor, wherein the inner-diffusion layer is disposed above the inner-contact layer relative to the normal force received thereon.

18. The method of claim 17, further comprising normalizing the normal forces through the inner-diffusion layer at the plurality of locations across the inner-diffusion layer, and receiving the normal forces across the surface area of the sensing layer, wherein the sensing layer is disposed above the inner-contact layer and the inner-diffusion layer relative to the normal force received thereon.

19. The method of claim 15, wherein the outer-diffusion layer and the inner-diffusion layer include a greater elasticity than the outer-contact layer and the inner-contact layer such that the outer-diffusion layer and the inner-diffusion layer are flexible relative to the outer-contact layer and the inner-contact layer.

20. A glove apparatus comprising:
a glove system to be worn by a user, the glove system including at least one finger surface region and a palmar surface region;
a plurality of sensors provided on at least one of the at least one finger surface region and the palmer surface region, each of the plurality of sensors including:
an outer layer positioned along a surface of the glove apparatus and configured to receive a force from the surface of the glove apparatus, the force including a horizontal component and a vertical component, the outer layer is further configured to distribute the force and normalize the distributed force therethrough by transitioning the force into a scalar force including the vertical component of the force; and
an inner layer positioned opposite to the outer layer and configured to receive a normal force in response to the outer layer receiving the force at the surface of the glove apparatus, the inner layer is further configured to distribute the normal force and normalize the distributed normal force therethrough; and
a sensing layer disposed between the outer layer and the inner layer, the sensing layer is configured to receive the scalar force from the outer layer and the scalar normal force from the inner layer to detect a resultant magnitude of the force received from the surface of the glove apparatus,
wherein the outer layer includes an outer-contact layer and an outer-diffusion layer,
wherein the inner layer includes an inner-contact layer and an inner-diffusion layer,
wherein the inner-contact layer has a greater elasticity than the outer-contact layer, and
wherein the inner-diffusion layer has a greater elasticity than the outer-diffusion layer.

21. The glove apparatus of claim 20, wherein the outer layer includes a first thickness having a first Shore Hardness value of about 75 A to 95 A and a second thickness having a second Shore Hardness value of about 27 A to about 50 A.

22. The glove apparatus of claim 21, wherein the first thickness of the outer layer is positioned proximate to the surface of the glove apparatus relative to the second thickness, and the second thickness of the outer layer is positioned proximate to the sensing layer relative to the first thickness.

23. The glove apparatus of claim 20, wherein the outer-diffusion layer and the inner-diffusion layer include a greater elasticity than the outer-contact layer and the inner-contact layer such that the outer-diffusion layer and the inner-diffusion layer are flexible relative to the outer-contact layer and the inner-contact layer.

* * * * *

UNITED STATES PATENT AND TRADEMARK OFFICE
CERTIFICATE OF CORRECTION

PATENT NO. : 11,041,772 B2
APPLICATION NO. : 16/363135
DATED : June 22, 2021
INVENTOR(S) : Benjamin Atkinson, Caleb Rogers and Tyler Flood Page 1 of 1

It is certified that error appears in the above-identified patent and that said Letters Patent is hereby corrected as shown below:

In the Specification

In Column 13, Line(s) 63, delete "Hardnes" and insert --Hardness--, therefor.

In Column 16, Line(s) 35, delete "corresponaence" and insert --correspondence--, therefor.

In Column 16, Line(s) 35, delete "aistributions" and insert --distributions--, therefor.

In Column 16, Line(s) 60, delete "distributea" and insert --distributed--, therefor.

In Column 17, Line(s) 35, delete "distrubuted" and insert --distributed--, therefor.

In Column 17, Line(s) 35, after "across", delete "tne" and insert --the--, therefor.

In Column 17, Line(s) 48, delete "tne" and insert --the--, therefor.

In Column 17, Line(s) 58, delete "tne" and insert --the--, therefor.

In Column 17, Line(s) 66, delete "distributea" and insert --distributed--, therefor.

Signed and Sealed this
Third Day of August, 2021

Drew Hirshfeld
*Performing the Functions and Duties of the
Under Secretary of Commerce for Intellectual Property and
Director of the United States Patent and Trademark Office*